(12) United States Patent
Wang et al.

(10) Patent No.: US 8,348,937 B2
(45) Date of Patent: Jan. 8, 2013

(54) IRRIGATED ABLATION CATHETER

(75) Inventors: Huisun Wang, Maple Grove, MN (US); Harry A. Puryear, Shoreview, MN (US); Stephen W. Evans, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 794 days.

(21) Appl. No.: 12/347,150

(22) Filed: Dec. 31, 2008

(65) Prior Publication Data
US 2010/0168728 A1    Jul. 1, 2010

(51) Int. Cl.
*A61B 18/18*    (2006.01)

(52) U.S. Cl. ......................................................... 606/41

(58) Field of Classification Search ............... 606/41, 606/31
See application file for complete search history.

(56) References Cited

U.S. PATENT DOCUMENTS

| | | | |
|---|---|---|---|
| 5,098,431 A | 3/1992 | Rydell | |
| 5,242,441 A | 9/1993 | Avitall | |
| 5,327,889 A | 7/1994 | Imran | |
| 5,843,152 A * | 12/1998 | Tu et al. ........................ | 607/122 |
| 5,906,613 A * | 5/1999 | Mulier et al. ................... | 606/41 |
| 5,913,854 A * | 6/1999 | Maguire et al. ................. | 606/41 |
| 6,063,080 A | 5/2000 | Nelson et al. | |
| 6,245,066 B1 | 6/2001 | Morgan et al. | |
| 6,866,662 B2 | 3/2005 | Fuimaono et al. | |
| 7,156,843 B2 | 1/2007 | Skarda | |
| 7,207,989 B2 | 4/2007 | Pike et al. | |
| 7,241,295 B2 | 7/2007 | Maguire | |
| 7,276,061 B2 | 10/2007 | Schaer et al. | |
| 7,311,708 B2 * | 12/2007 | McClurken ..................... | 606/50 |
| 7,340,307 B2 | 3/2008 | Maguire et al. | |
| 7,393,353 B2 | 7/2008 | Hooven | |
| 7,410,486 B2 | 8/2008 | Fuimaono et al. | |
| 7,537,595 B2 * | 5/2009 | McClurken ..................... | 606/50 |
| 8,052,684 B2 * | 11/2011 | Wang et al. ..................... | 606/49 |
| 2003/0195478 A1 | 10/2003 | Russo et al. | |
| 2005/0090816 A1 * | 4/2005 | McClurken et al. ............ | 606/41 |
| 2005/0119651 A1 | 6/2005 | Fuimaono et al. | |
| 2006/0064065 A1 | 3/2006 | Russo et al. | |
| 2006/0122593 A1 * | 6/2006 | Jun ................................. | 606/41 |
| 2006/0184165 A1 | 8/2006 | Webster et al. | |
| 2006/0199999 A1 | 9/2006 | Ikeda et al. | |
| 2007/0270791 A1 * | 11/2007 | Wang et al. ..................... | 606/41 |
| 2008/0071267 A1 * | 3/2008 | Wang et al. ..................... | 606/41 |
| 2008/0091193 A1 * | 4/2008 | Kauphusman et al. ......... | 606/41 |
| 2008/0119694 A1 | 5/2008 | Lee | |
| 2008/0147046 A1 | 6/2008 | McDaniel | |
| 2008/0161792 A1 | 7/2008 | Wang et al. | |
| 2008/0161793 A1 | 7/2008 | Wang et al. | |
| 2008/0161794 A1 * | 7/2008 | Wang et al. ..................... | 606/41 |
| 2008/0161795 A1 * | 7/2008 | Wang et al. ..................... | 606/41 |
| 2008/0161797 A1 * | 7/2008 | Wang et al. ..................... | 606/41 |
| 2008/0161800 A1 * | 7/2008 | Wang et al. ..................... | 606/41 |
| 2008/0183128 A1 | 7/2008 | Morriss et al. | |
| 2008/0249463 A1 | 10/2008 | Pappone et al. | |
| 2008/0249522 A1 | 10/2008 | Pappone et al. | |

* cited by examiner

*Primary Examiner* — Nicholas Lucchesi
*Assistant Examiner* — Diva K Chander
(74) *Attorney, Agent, or Firm* — Armstrong Teasdale LLP (57) ABSTRACT

An irrigated ablation catheter includes a tubular catheter body having an inner tubular member and an outer tubular member. The catheter body has a proximal portion and a distal portion. The catheter also includes an electrode extending from the distal portion of the catheter body, a flow distributor positioned at least partially within distal portion of the catheter body and at least partially overlapping the electrode, and a flow path extending through the catheter body and the flow distributor. The flow path is configured to provide cooling fluid to an external surface of the electrode.

26 Claims, 8 Drawing Sheets

IRRIGATED ABLATION CATHETER

BACKGROUND OF THE INVENTION

1. Field of the Invention

The field of the invention relates generally to ablation catheters and, more particularly, to irrigated ablation catheters having a flow distributor that dispenses the fluid from a distal portion of the catheter.

2. Background Art

Electrophysiology catheters are used for an ever-growing number of procedures. For example, catheters are used for diagnostic, therapeutic, and ablative procedures, to name just a few examples. Typically, the catheter is manipulated through the patient's vasculature to the intended site, for example, a site within the patient's heart.

The catheter typically carries one or more electrodes, which may be used for ablation, diagnosis, or the like. There are a number of methods used for ablation of desired areas, including for example, radiofrequency (RF) ablation. RF ablation is accomplished by transmission of radiofrequency energy to a desired target area through an electrode assembly to ablate tissue at the target site.

Because RF ablation may generate significant heat, it is desirable to monitor the temperature of the ablation assembly. It is further desirable to include a mechanism to irrigate certain target areas with biocompatible fluids, such as saline solution. This irrigation reduces or avoids excess, unwanted tissue damage, and blood coagulation and problems associated therewith. However, introduction of this irrigation solution may inhibit the ability to accurately monitor and/or control the temperature of the ablation assembly during use.

Open ablation catheters typically deliver the cooling fluid through open orifices on the electrode. The current open irrigated ablation catheters use the inner cavity of the electrode, or distal member, as a manifold to distribute saline solution. The saline flows directly through the open orifices of the distal electrode member. This direct flow through the distal electrode member lowers the temperature of the electrode member during operation, rendering accurate monitoring and control of the ablative process more difficult.

BRIEF DESCRIPTION OF THE INVENTION

In one aspect, an irrigated ablation catheter is provided that includes a tubular catheter body having an inner tubular member and an outer tubular member. The catheter body has a proximal portion and a distal portion. The catheter also includes an electrode extending from the distal portion of the catheter body, a flow distributor positioned at least partially within the distal portion of the catheter body and at least partially overlapping the electrode, and a flow path extending through the catheter body and the flow distributor. The flow path is configured to provide cooling fluid to an external surface of the electrode.

In another aspect, an electrode assembly is provided for an irrigated ablation catheter. The assembly includes an electrode having a proximal portion, a distal portion, and a passageway extending through the distal portion. The electrode also includes a manifold body contacting a proximal portion of the electrode, and a distal tube extending from the manifold body through the electrode passageway.

In another aspect, an irrigated ablation catheter is provided that includes a tubular catheter body having an inner tubular member and an outer tubular member. The catheter body includes a proximal portion and a distal portion. The catheter also includes an electrode extending from the distal portion of the catheter body, a flow member positioned at least partially within the distal portion of the catheter body, and a flow path extending through the catheter body and the member to an outside of the catheter. The flow path is configured to provide cooling fluid to an external surface of the electrode.

In another aspect, a method is provided for assembling an electrode assembly for an ablation catheter. The assembly includes an electrode, a manifold body, and a distal tube. The method includes loading the distal tube onto a mandrel, inserting the mandrel and the distal tube through a distal cavity of the manifold body until a proximal end of the distal tube is positioned adjacent an end of the distal cavity, and positioning the electrode over the mandrel and the distal tube.

DETAILED DESCRIPTION OF THE INVENTION

The invention set forth below in detail is an irrigated ablation catheter. The catheter provides irrigation fluid to an electrode assembly located at a distal end thereof. The catheter is a multi-tube catheter and fluid is directed through one of the tubes of the catheter. The fluid is dispersed from a distal portion of the catheter to provide sufficient cooling to prevent coagulation of blood while not overcooling the electrode assembly. In an exemplary embodiment, the fluid exits the distal portion of the catheter and flows around the external surface of an electrode to cool the area immediately surrounding the electrode. In one embodiment, the electrode assembly is a single piece unit. In alternative embodiments, the electrode assembly includes a multi-piece manifold assembly including a distal tube attached to a manifold body. In some embodiments, the tube is bonded to the body and/or the electrode and in other embodiments, the tube is press fit onto the body and/or the electrode.

The systems and methods set forth below are not limited to the specific embodiments described herein. In addition, components of each system and steps of each method can be practiced independently and separately from other components and method steps described herein. Each component and method step also can be used in combination with other catheters, electrodes, systems, and methods.

As used herein, "proximal" refers to the direction away from the body of a patient and towards a clinician. Further-more, as used herein, "distal" refers to the direction toward the body of a patient and away from the clinician.

Figure 1:
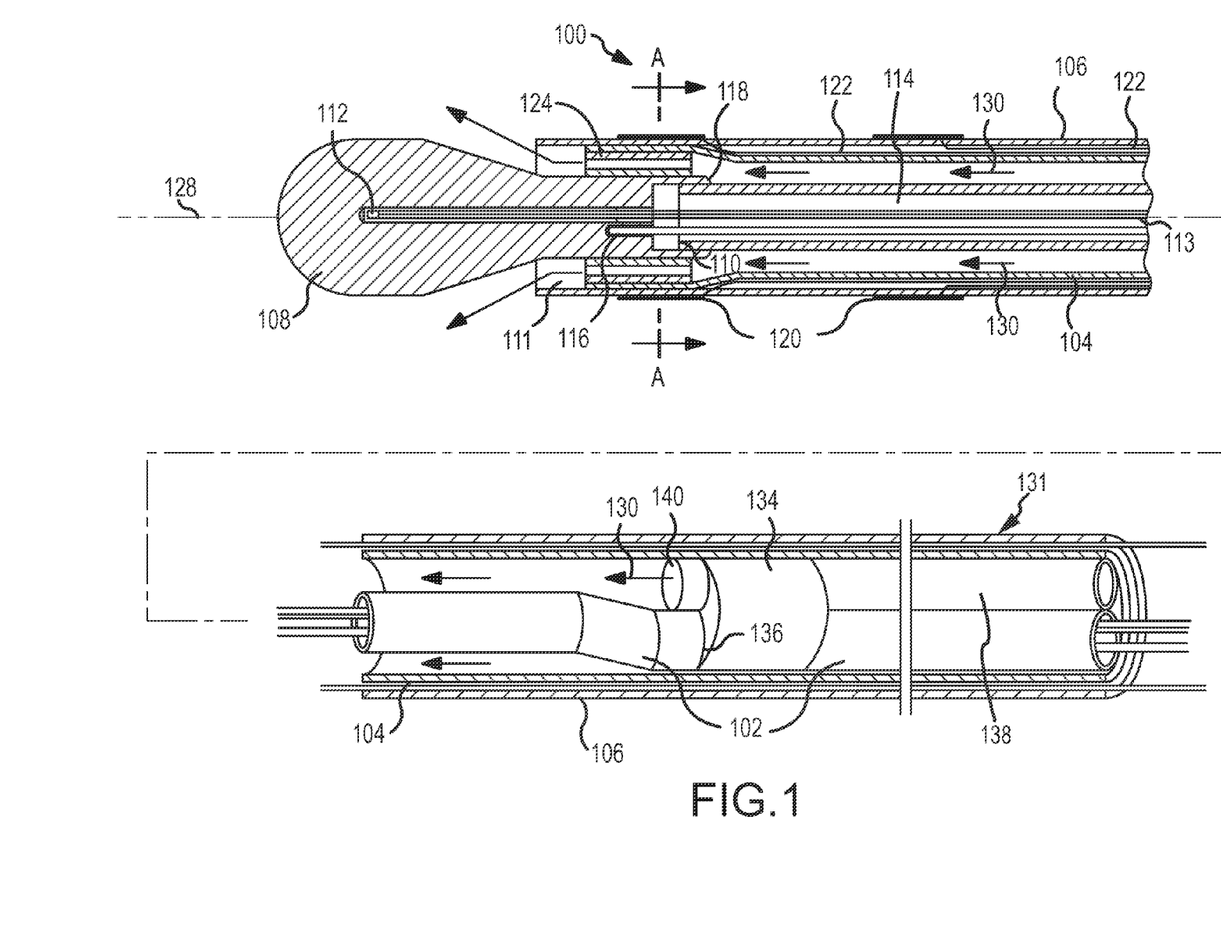
FIG. 1 is schematic view of an ablation catheter in accordance with one embodiment of the invention.

FIG. 1 illustrates a distal portion of an ablation catheter 100 in accordance with one embodiment of the invention. Catheter 100 includes an inner tubular member 102, a middle tubular member 104, and an outer tubular member 106. Catheter 100 also includes an electrode 108 extending from a distal end 110 of inner tubular member 102. In one embodiment, electrode 108 is manufactured from any electro-conductive material suitable for medical use. In the exemplary embodiment, electrode 108 is manufactured from a platinum-iridium alloy and typically is 4 mm in length. Alternatively, electrode 108 is manufactured from one or more of gold, a gold alloy, a noble metal, stainless steel, platinum, and iridium and has a length from about 2.5 mm to about 6 cm. In a further embodiment, electrode 108 includes an electro-conductive coating.

In the illustrated embodiment, a proximal portion of electrode 108 has a diameter that is slightly larger than a diameter of inner tubular member 102. A cavity is formed within the proximal portion of electrode 108 and distal end 110 of inner tubular member 102 is positioned within the cavity. The outer diameter of electrode 108 increases from the proximal portion of electrode 108 to about a middle of electrode 108, and then has a rounded configuration to a distal end of electrode 108. Thus, electrode 108 has a necked proximal portion that enlarges to a bulbous shaped distal portion. In one embodiment, this shape is referred to as a tear drop shape. This shape allows cooling fluid to pass within a gap 111 that extends between the outer surface of electrode 108 and both middle tubular member 104, and outer tubular member 106.

Electrode 108 includes at least one temperature sensing mechanism 112 located therewithin. Temperature sensing mechanism 112 is operatively connected to an RF generator located outside of the body by wires 113. Wires 113 extend through a lumen 114 within inner tubular member 102 from electrode 108 to a proximal portion of catheter 100. Temperature sensing mechanism 112 is utilized to monitor a temperature of electrode 108. Electrode 108 also includes an RF power wire 116 that extends into a proximal portion of electrode 108 and provides the power utilized to heat electrode 108. Wire 116 extends through lumen 114 from a proximal portion of electrode 108 to a proximal portion of catheter 100.

In one embodiment, electrode 108 is bonded to distal end 110 of inner tubular member 102 with a bonding agent 118. In an alternative embodiment, electrode 108 is press fit onto distal end 110 of inner tubular member 102. As shown in FIG. 1, electrode 108 is a single piece member and catheter 100 does not include a manifold connecting electrode 108 with tubular member 102. Rather, tubular members 102 and 104 provide the flow path for cooling fluid within catheter 100. Alternative embodiments of electrode assemblies are shown in FIGS. 8-12 and are described below in greater detail. Such alternative embodiments include assemblies having multiple piece manifolds that connect the electrode with a tubular member.

Catheter 100 also includes at least one sensing ring 120 attached to a distal portion of outer tubular member 106. A wire 122 extends from each sensing ring through catheter 100 to a power source (not shown). In one embodiment, the power source is the RF generator. In the embodiment illustrated in FIG. 1, wire 122 extends through catheter 100 in the space between outer tubular member 106 and middle tubular member 104.

Figure 2:
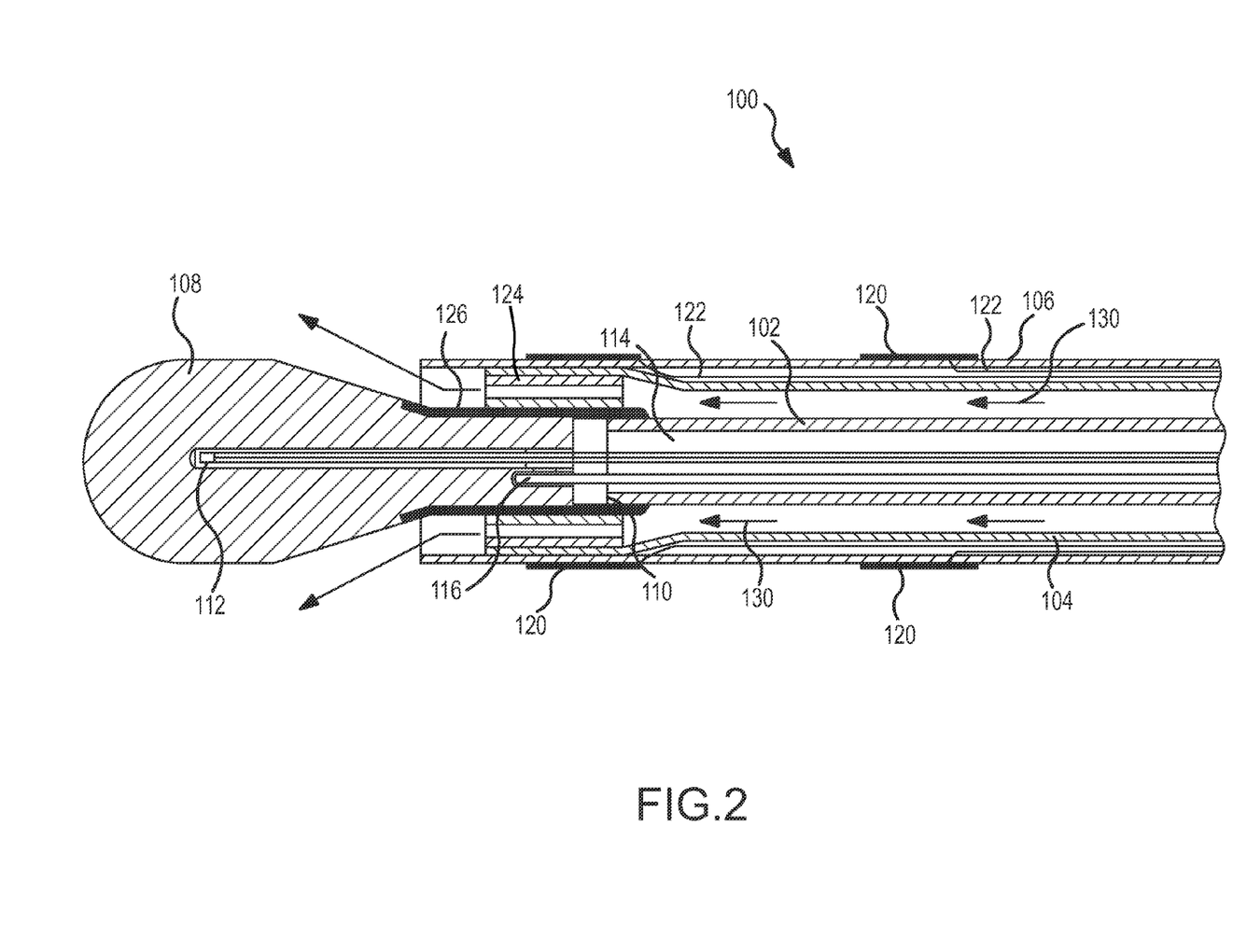
FIG. 2 is a schematic view of the ablation catheter shown in FIG. 1 including an insulation member on a proximal portion of the electrode.

Catheter 100 also includes a flow distributor 124 positioned at least partially within a distal portion of catheter 100. More specifically, flow distributor 124 is positioned at least partially within middle tubular member 104. In the exemplary embodiment, flow distributor 124 is bonded, or press fit, to an internal surface of middle tubular member 104 and to an outer surface of electrode 108, and is positioned between a proximal end of electrode 108 and a distal end of outer tubular member 106. Flow distributor 124 overlaps at least a portion of electrode 108. Alternatively, as shown in FIG. 2, flow distributor 124 is bonded to an insulating member 126 (shown in FIG. 2) that is positioned on a proximal portion of electrode 108. In this alternative embodiment, insulating member 126 is fabricated from a poor thermally conductive polymer such as polyether ether ketone (PEEK) and is fit and/or bonded onto electrode 108. Insulating member 126 is configured to minimize cooling fluid contact with a proximal portion of electrode 108 to provide for more even temperature control of electrode 108 during an ablation procedure. As shown in FIGS. 1 and 2, electrode 108 is at least partially within flow distributor 124. Additionally, electrode 108 is positioned partially within, and extends from, the distal portion of catheter 100.

Catheter 100 includes an axis 128 and a flow path 130 that extends from a proximal end 131 of catheter 100 to a distal end 132 of catheter 100. Flow path 130 extends through catheter 100 in the space between inner tubular member 102 and middle tubular member 104. A distal end of middle tubular member 104 is attached to a distal portion of outer tubular member 106 proximally from a distal end of outer tubular member 106. Accordingly, although flow path 130 extends mostly within middle tubular member 104, as it continues distally beyond middle tubular member 104, it extends through outer tubular member 106 such that a portion of the fluid contacts an inner surface of outer tubular member 106.

Catheter 100 also includes a seal member 134 located in a proximal portion of catheter 100. Seal member 134 includes a pair of openings therethrough, and in one embodiment, seal member 134 has a cylindrical shape, although it can be any shape. Inner tubular member 102 extends through a first opening 136 and a fluid supply tube 138 extends through a second opening 140. Fluid supply tube 138 delivers fluid to second opening 140, and seal member 134 prevents fluid from entering lumen 114 within inner tubular member 102 and the space between middle tubular member 104 and outer tubular member 106. Seal member 134 transfers the fluid from an inner fluid delivery lumen of fluid supply tube 138 to the space between inner tubular member 102 and middle tubular member 104. In one embodiment, seal member 134 is fabricated from polymeric materials, such as plastic materials including one or more of polyurethane, a polyether resin such as Pebax® (available from Arkema), and adhesive materials.

Figure 3:
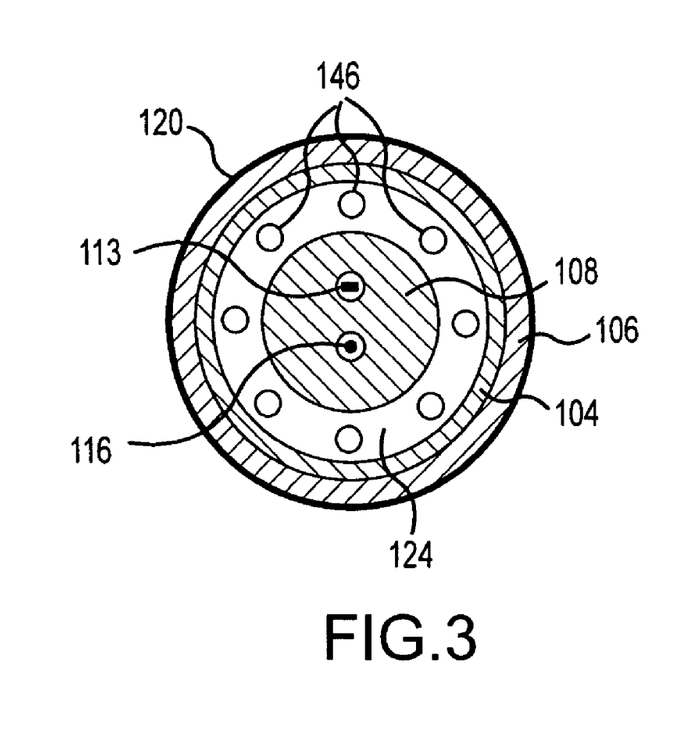
FIG. 3 is a cross-sectional view along A-A shown in FIG. 1 depicting a flow distributor having passageways.

FIG. 3 is a cross-sectional view along line A-A shown in FIG. 1 of an exemplary flow distributor 124. Flow distributor 124 is a tubular member with passageways 146 extending parallel to axis 128 (shown in FIG. 1). In the embodiment illustrated in FIG. 3, passageways 146 have a circular cross-section. Passageways 146 allow fluid to flow from the space between inner tubular member 102 (shown in FIG. 1) and middle tubular member 104 (shown in FIG. 1) to an outside of catheter 100 (shown in FIG. 1) and cool electrode 108 (shown in FIG. 1).

Figure 4:
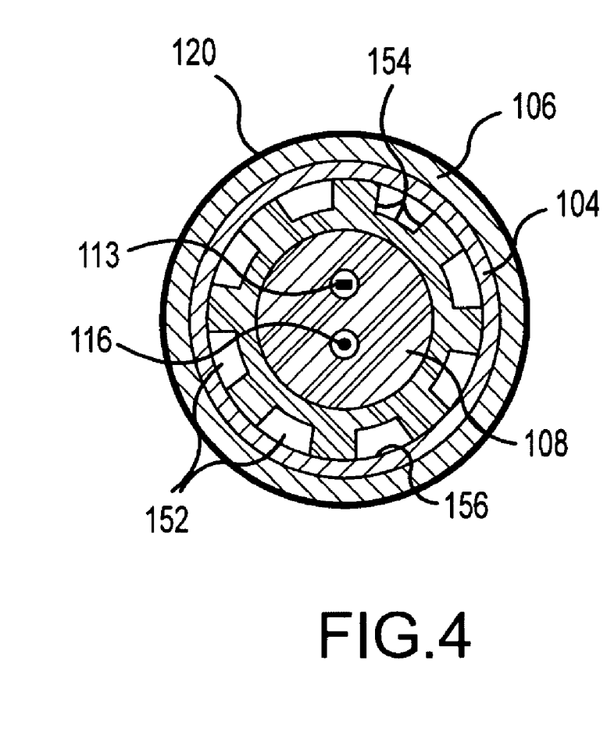
FIG. 4 is a cross-sectional view along A-A shown in FIG. 1 depicting an alternative flow distributor having channels.
Figures 5, 6:
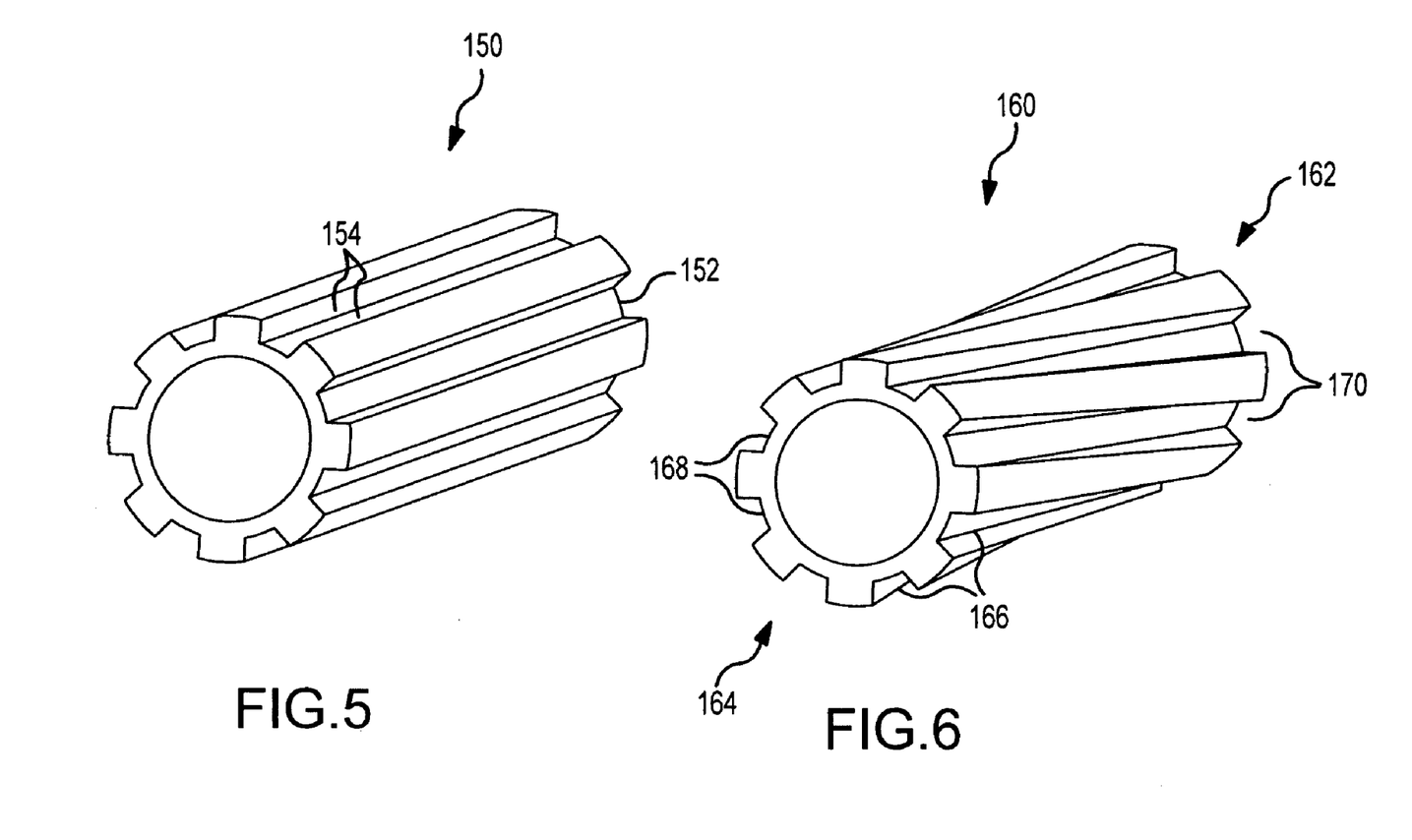
FIG. 5 is a perspective view of the flow distributor shown in FIG. 4.
FIG. 6 is a perspective view of an alternative flow distributor.

FIGS. 4 and 5 illustrate an alternative flow distributor 150. FIG. 4 is a cross-sectional view along line A-A shown in FIG. 1 of flow distributor 150. Flow distributor 150 is a tubular member with channels, or grooves, 152 extending parallel to axis 128 (shown in FIG. 1). Channels 152 allow fluid to flow from the space between inner tubular member 102 (shown in FIG. 1) and middle tubular member 104 (shown in FIG. 1) to an outside of catheter 100 (shown in FIG. 1) and cool electrode 108 (shown in FIG. 1). As shown in FIG. 5, channels 152 extend longitudinally along an outside of flow distributor 150 such that fluid flows between, and contacts, channel walls 154 and an interior surface 156 of middle tubular member 104.

Figure 7:
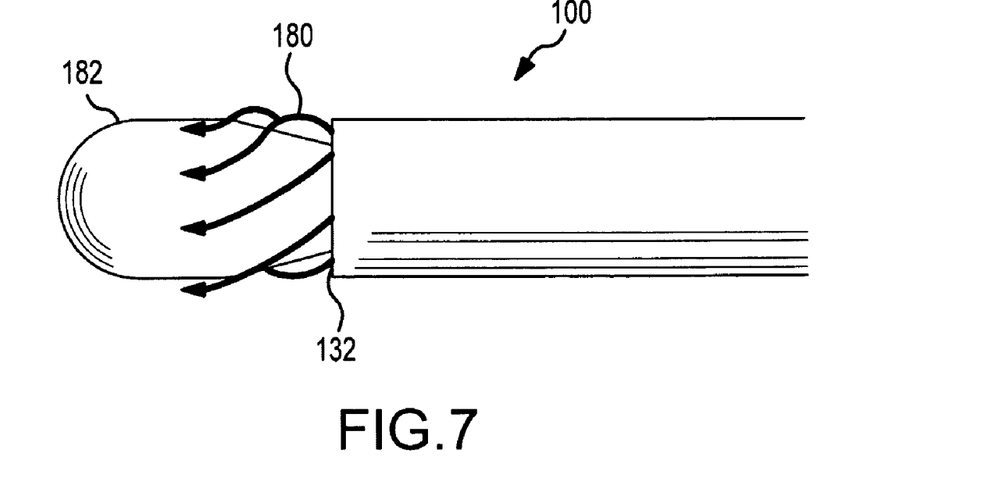
FIG. 7 is a schematic view of a swirled fluid flow as it is dispensed through a flow distributor such as the flow distributor shown in FIG. 6.

FIG. 6 illustrates a perspective view of a further alternative flow distributor 160 having a proximal end 162 and a distal end 164. A plurality of channels 166 extend from proximal end 162 to distal end 164. As shown in FIG. 6, distal channel ends 168 are circumferentially displaced with regard to proximal channel ends 170. In one embodiment, the circumferential displacement is between about 0 and 60 degrees. Specifically, the circumferential displacement is between about 20 and 45 degrees. More specifically, the circumferential displacement is between about 30 and 40 degrees. The circumferentially displaced ends of flow distributor 160 disperse the fluid in a swirling manner 180 as illustrated in FIG. 7. Upon the fluid exiting distal end 132 of catheter 100, the fluid swirls 180 about an external surface 182 of electrode 108, displacing bodily fluids in that proximity, and cooling external surface 182 of electrode 108. This distally directed swirling 180 of the fluid allows for increased cooling efficiency which decreases the likelihood of thrombus formation during an ablation procedure. In a further alternative embodiment, passageways 146 (shown in FIG. 3) are circumferentially displaced between a proximal end of flow distributor 124 and a distal end of flow distributor 124.

Figure 8:
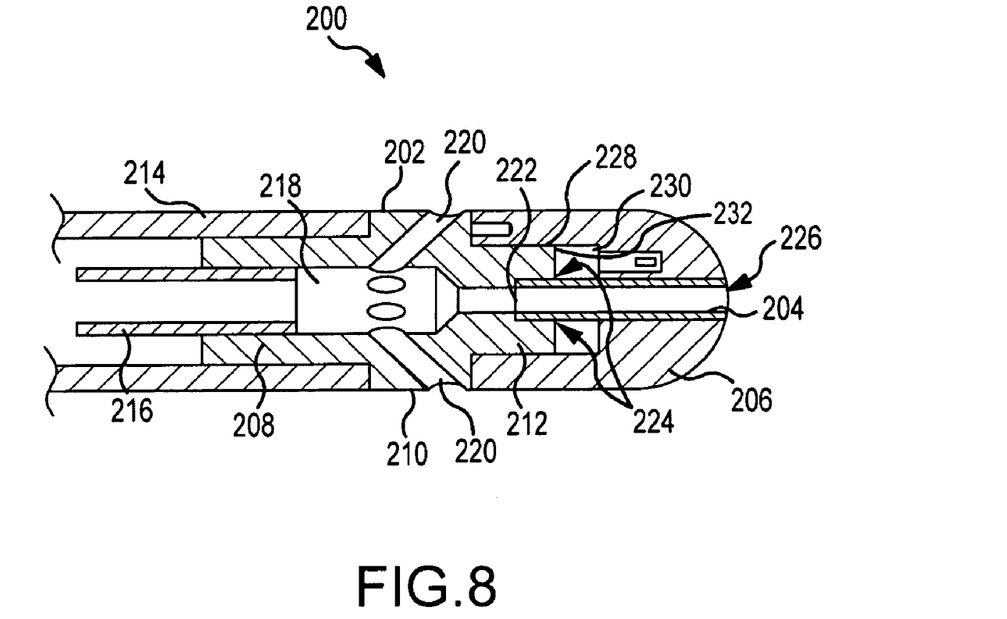
FIG. 8 is a schematic view of an alternative electrode assembly.

FIG. 8 illustrates an alternative electrode assembly 200 that includes a manifold body 202, a distal tube 204, and an electrode member 206. Manifold body 202 includes a proximal portion 208, a middle portion 210, and a distal portion 212. An outer tubular member 214 of a catheter is attached to manifold proximal portion 208 and is positioned adjacent manifold middle portion 210. An inner tubular member 216 delivers fluid to manifold body 202 and is attached to proximal portion 208 of manifold body 202. Manifold body 202 has a proximal cavity 218 formed therein from a proximal end of proximal portion 208. Inner tubular member 216 is fitted at least partially within cavity 218. A plurality of passageways 220 extend from cavity 218 radially outward and through manifold middle portion 210 to form a flow path. The passageways are angled distally such that a cooling fluid flows both radially outward and distally as it passes through passageways 220. The flow path extends through inner tubular member 216, through cavity 218 and passageways 220, and then out manifold body 202 such that a cooling fluid circulates about electrode 206. In a further embodiment, passageways 220 are circumferentially displaced between a proximal end and a distal end thereof such that the fluid swirls about electrode 206 (as shown in FIG. 7).

Distal tube 204 extends distally from a distal cavity 222 within distal manifold body portion 212. In the embodiment illustrated in FIG. 8, distal tube 204 is bonded to distal manifold body portion 212 with a bonding agent 224. Distal tube 204 extends distally through a passageway 226 which extends distally through electrode 206. A cavity 228 formed within electrode 206 accommodates distal portion 212 of manifold body 202 and a gap 230 is formed between electrode 206 and a distal end 232 of distal manifold portion 212. In one embodiment, bonding agent 224 is located at least partially within gap 230.

Figure 9:
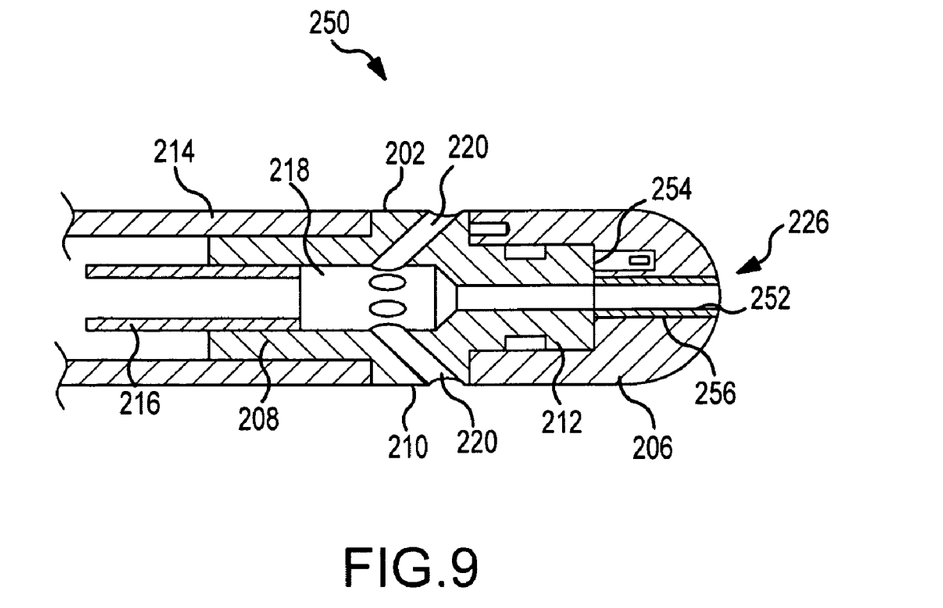
FIG. 9 is a schematic view of a further alternative electrode assembly.

FIG. 9 illustrates an alternative electrode assembly 250 in which like reference numerals refer to similar elements shown in FIG. 8. Assembly 250 includes manifold body 202, a distal tube 252, and electrode member 206. Manifold body 202 includes proximal portion 208, middle portion 210, and distal portion 212. Outer tubular member 214 of a catheter is attached to manifold proximal portion 208 and is positioned adjacent manifold middle portion 210. Inner tubular member 216 delivers fluid to manifold body 202 and is attached to proximal portion 208 of manifold body 202. Proximal cavity 218 is formed in manifold body 202 from a proximal end of proximal portion 208. Inner tubular member 216 is fitted at least partially within cavity 218. Passageways 220 extend from cavity 218 radially outward and through manifold middle portion 210 to form the flow path. Passageways 220 are angled distally such that cooling fluid flows both radially outward and distally as it passes through passageways 220. The flow path extends through inner tubular member 216, through cavity 218 and passageways 220 and then out manifold body 202 such that the cooling fluid circulates about electrode 206. In a further embodiment, passageways 220 are circumferentially displaced between a proximal end and a distal end thereof such that the fluid swirls about electrode 206 (as shown in FIG. 7).

Distal tube 252 contacts a distal end 254 of manifold body distal portion 212 and extends distally therefrom. In the embodiment illustrated in FIG. 9, a sidewall 256 of distal tube 204 is bonded to electrode 206 with a bonding agent (not shown). Distal tube 252 extends distally through passageway 226 which extends distally through electrode 206. Cavity 228 which is formed within electrode 206 accommodates distal portion 212 of manifold body 202.

Figure 10:
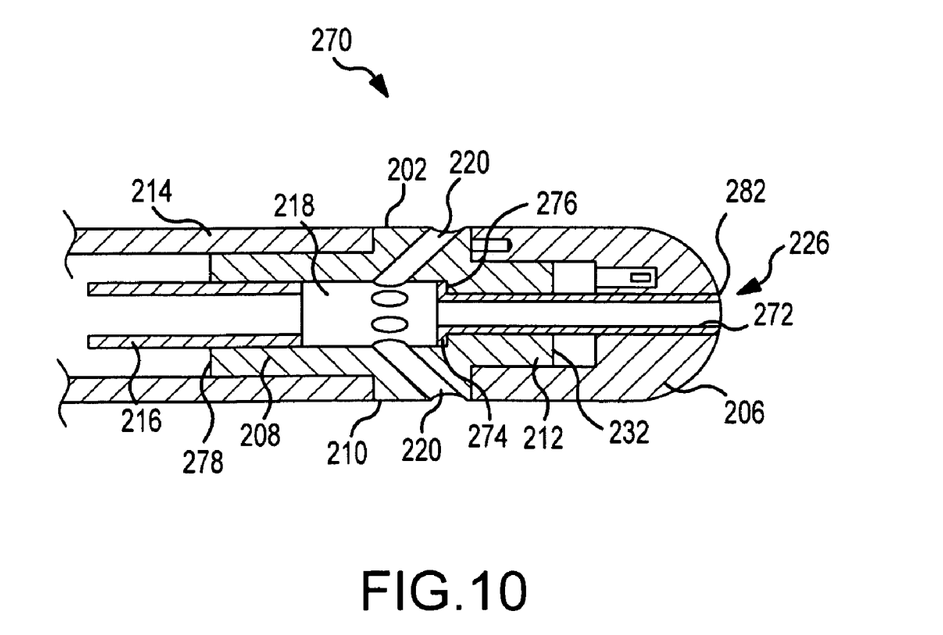
FIG. 10 is a schematic view of a further alternative electrode assembly.

FIG. 10 illustrates a further alternative embodiment of an electrode assembly 270 in which like reference numerals refer to similar elements. Assembly 270 includes manifold body 202, a distal tube 272, and electrode member 206. Manifold body 202 includes proximal portion 208, middle portion 210, and distal portion 212. Outer tubular member 214 of a catheter is attached to manifold proximal portion 208 and is positioned adjacent manifold middle portion 210. Inner tubular member 216 delivers fluid to manifold body 202 and is attached to proximal portion 208 of manifold body 202. Proximal cavity 218 is formed in manifold body 202 from a proximal end of proximal portion 208. Inner tubular member 216 is fitted at least partially within cavity 218. Passageways 220 extend from cavity 218 radially outward and through manifold middle portion 210 to form the flow path. Passageways 220 are angled distally such that cooling fluid flows both radially outward and distally as it passes through passageways 220. The flow path extends through inner tubular member 216, through cavity 218 and passageways 220 and then out manifold body 202 such that the cooling fluid circulates about electrode 206. In a further embodiment, passageways 220 are circumferentially displaced between a proximal end and a distal end thereof such that the fluid swirls about electrode 206 (as shown in FIG. 7).

Distal tube 272 extends from manifold body proximal cavity 218 through manifold body distal cavity 222, cavity 228, and passageway 226. Distal tube 272 includes a flared end, or flange 274 that contacts a distal inner surface 276 of proximal cavity 218. Thus, during assembly, distal tube 272 is inserted through manifold body 202 from a proximal end 278 towards distal end 232. A distal end 282 of distal tube 272 extends through manifold body 202 until flange 274 contacts inner surface 276.

Figure 11:
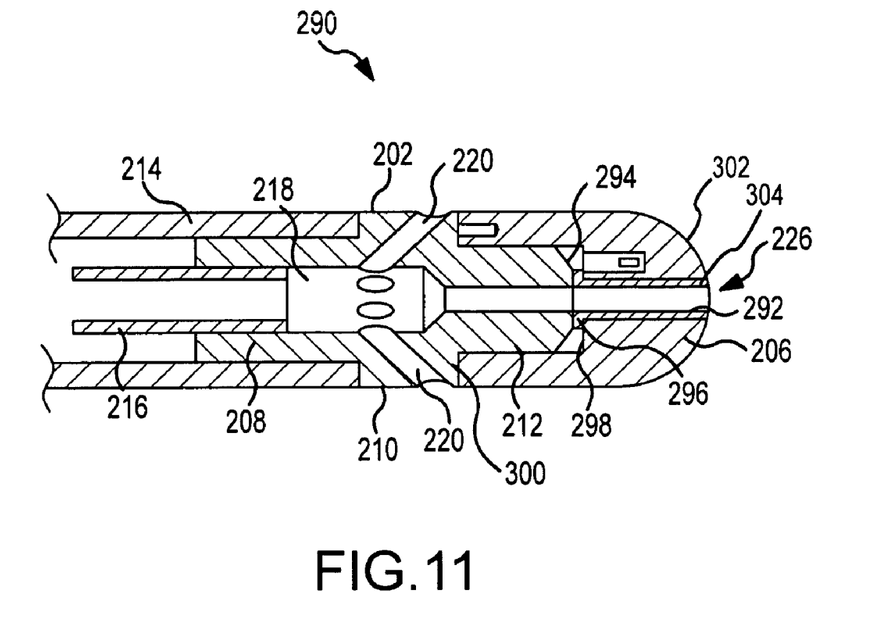
FIG. 11 is a schematic view of a further alternative electrode assembly.

FIG. 11 illustrates a further alternative embodiment of an electrode assembly 290 in which like reference numerals refer to similar elements. Assembly 290 includes manifold body 202, a distal tube 292, and electrode member 206. Manifold body 202 includes proximal portion 208, middle portion 210, and distal portion 212. Outer tubular member 214 of a catheter is attached to manifold proximal portion 208 and is positioned adjacent manifold middle portion 210. Inner tubular member 216 delivers fluid to manifold body 202 and is attached to proximal portion 208 of manifold body 202. Proximal cavity 218 is formed in manifold body 202 from a proximal end of proximal portion 208. Inner tubular member 216 is fitted at least partially within cavity 218. Passageways 220 extend from cavity 218 radially outward and through manifold middle portion 210 to form the flow path. Passageways 220 are angled distally such that cooling fluid flows both radially outward and distally as it passes through passageways 220. The flow path extends through inner tubular member 216, through cavity 218 and passageways 220 and then out manifold body 202 such that the cooling fluid circulates about electrode 206. In a further embodiment, passageways 220 are circumferentially displaced between a proximal end and a distal end thereof such that the fluid swirls about electrode 206 (as shown in FIG. 7).

Distal tube 292 contacts a distal end 294 of manifold body 202 and extends from electrode cavity 228 through passageway 226. Distal tube 292 includes a flared end, or flange 296 that contacts a distal inner surface 298 of proximal cavity 218. During assembly, distal tube 292 is inserted through electrode cavity 228 from a proximal end 300 towards a distal end 302 and a distal end 304 of distal tube 292 extends through electrode cavity 228 until flange 296 contacts inner surface 298. In the embodiment illustrated in FIG. 11, manifold body 202 has a tapered distal end 294.

Figure 12:
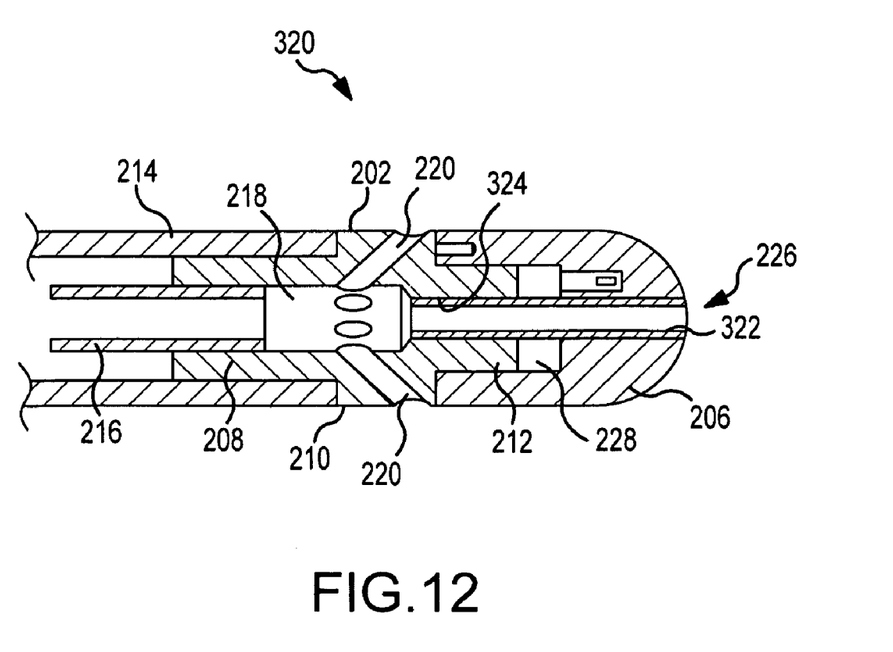
FIG. 12 is a schematic view of a further alternative electrode assembly.
Figure 13A:
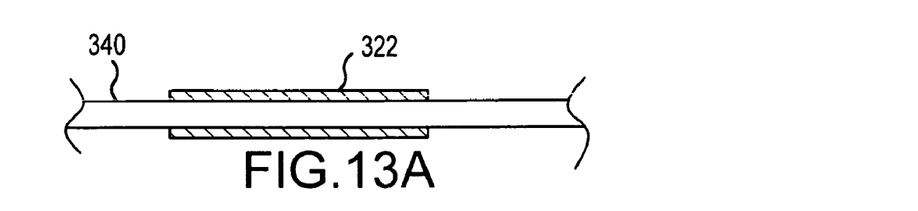
FIGS. 13A-E schematically illustrate the process of assembling the electrode assembly shown in FIG. 12.
Figure 13B:
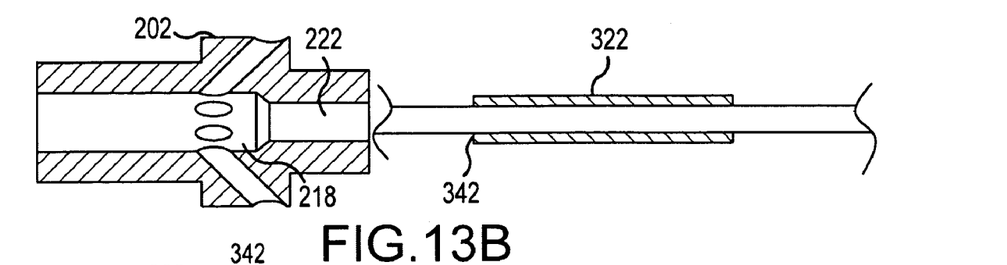
Figure 13C:
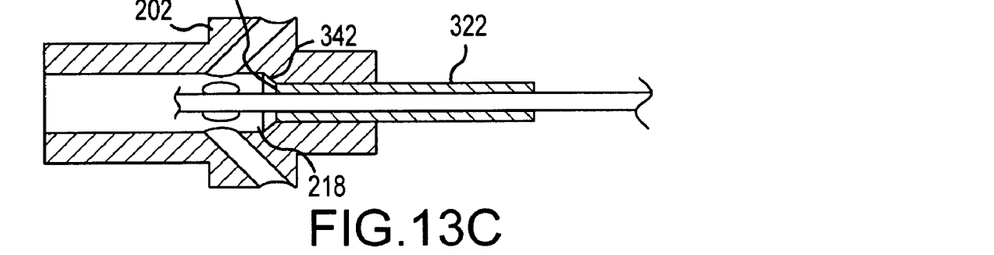
Figure 13D:
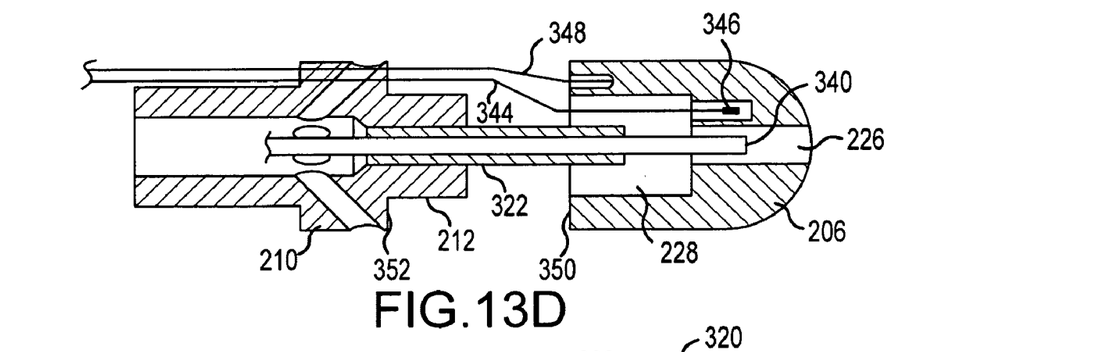
Figure 13E:
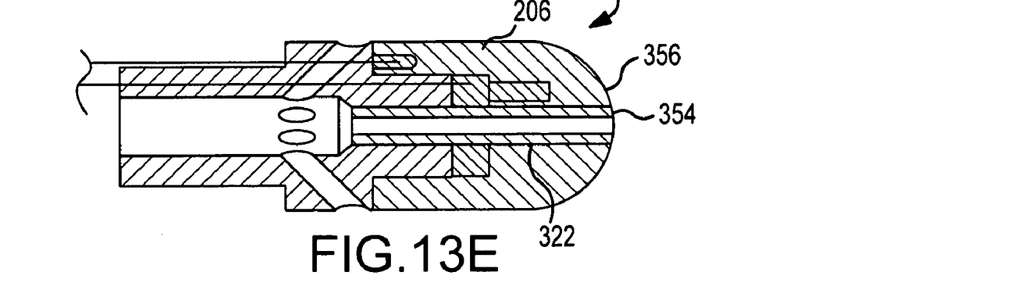

FIG. 12 illustrates a further alternative embodiment of an electrode assembly 320 in which like reference numerals refer to similar elements. Assembly 320 includes manifold body 202, a distal tube 322, and electrode member 206. Manifold body 202 includes proximal portion 208, middle portion 210, and distal portion 212. Outer tubular member 214 of a catheter is attached to manifold proximal portion 208 and is positioned adjacent manifold middle portion 210. Inner tubular member 216 delivers fluid to manifold body 202 and is attached to proximal portion 208 of manifold body 202. Proximal cavity 218 is formed in manifold body 202 from a proximal end of proximal portion 208. Inner tubular member 216 is fitted at least partially within cavity 218. Passageways 220 extend from cavity 218 radially outward and through manifold middle portion 210 to form the flow path. Passageways 220 are angled distally such that cooling fluid flows both radially outward and distally as it passes through passageways 220. The flow path extends through inner tubular member 216, through cavity 218 and passageways 220 and then out manifold body 202 such that the cooling fluid circulates about electrode 206. In a further embodiment, passageways 220 are circumferentially displaced between a proximal end and a distal end thereof such that the fluid swirls about electrode 206 (as shown in FIG. 7).

Distal tube 322 is press fit into manifold body distal cavity 222 against inside surface 324 of distal cavity 222. Distal tube 322 extends from adjacent manifold proximal cavity 218, through distal cavity 222, through electrode cavity 228, and through passageway 226 which passes through electrode 206.

FIGS. 13A-E schematically illustrate the process of assembling electrode assembly 320 (shown in FIG. 12). As shown in FIGS. 13A-13E, distal tube 322 is loaded onto a mandrel 340. Distal tube 322 is then inserted through distal cavity 222 of manifold body 202 until a proximal end 342 is positioned adjacent proximal cavity 218. Electrode 206 is then positioned over mandrel 340 and distal tube 322. Wires 344 connected to a thermocouple 346 and power wires 348 connected to electrode 206 are extended through, or around, manifold body 202. Electrode 206 is then positioned such that an electrode proximal end 350 contacts a distal end 352 of manifold body middle portion 210, manifold body distal portion 212 fits within electrode cavity 228, and distal tube 322 extends through passageway 226, until a distal end 354 of distal tube 322 is flush with a distal end 356 of electrode 206. In some embodiments, an adhesive is applied to distal tube 322 to maintain it in place both during the assembly process and during use of the catheter. Mandrel 340 is then removed from within distal tube 322 and electrode assembly 320.

Exemplary embodiments of catheters, electrode assemblies, and methods of assembly are described in detail above. The catheter, electrode assemblies, and methods are not limited to the specific embodiments described herein, but rather, components of the catheter and electrode assembly and/or steps of the methods may be utilized independently and separately from other components and/or steps described herein.

It is noted that the exemplary embodiments can be implemented and utilized in connection with many other ablation applications.

Although specific features of various embodiments of the invention are shown in some figures and not in others, this is for convenience only. In accordance with the principles of the invention, any feature of a figure may be referenced and/or claimed in combination with any feature of any other figure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An irrigated ablation catheter comprising:
   a tubular catheter body comprising an inner tubular member and an outer tubular member, said catheter body comprising a proximal portion and a distal portion;
   an electrode extending from said distal portion of said catheter body;
   a flow distributor positioned at least partially within said distal portion of said catheter body and at least partially overlapping said electrode, wherein said electrode is at least partially within said flow distributor; and
   a flow path extending through said catheter body and said flow distributor, said flow path configured to provide cooling fluid to an external surface of said electrode.

2. A catheter in accordance with claim 1 further comprising a middle tubular member having a distal end attached to a distal end of said outer tubular member, said flow path extending between said inner tubular member and said middle tubular member.

3. A catheter in accordance with claim 2 wherein said electrode is attached to a distal end of said inner tubular member, said flow distributor positioned at said middle tubular member distal end.

4. A catheter in accordance with claim 1 further comprising:
   a temperature sensor within said electrode; and
   at least one sensing ring located on an external surface of said outer tubular member.

5. A catheter in accordance with claim 2 further comprising a seal member configured to transfer the fluid from an inner fluid delivery lumen to the space between said inner tubular member and said middle tubular member.

6. A catheter in accordance with claim 1 further comprising an insulation member positioned on a proximal portion of said electrode, said insulation member having an inner surface and an outer surface, said inner surface contacting said electrode, said outer surface contacting said flow distributor.

7. A catheter in accordance with claim 1 wherein said catheter includes an axis and said flow distributor includes a plurality of channels extending therethrough, said channels being substantially parallel to said axis.

8. A catheter in accordance with claim 1 wherein said flow distributor includes a plurality of channels having a proximal end and a distal end, said distal end of said channels being circumferentially displaced with respect to said proximal end of said channels.

9. A catheter in accordance with claim 1 wherein said flowpath extends within a gap between a distal end of said outer tubular member and an outer surface of said electrode.

10. An electrode assembly for an irrigated ablation catheter, said assembly comprising:
- an electrode having a proximal portion, a distal portion, and a passageway extending through said distal portion;
- a manifold body contacting a proximal portion of said electrode; and
- a distal tube extending from said manifold body through said electrode passageway.

11. An assembly in accordance with claim 10 wherein said distal tube is at least one of bonded and press fit to said manifold body.

12. An assembly in accordance with claim 10 wherein said distal tube is at least one of bonded and press fit to said electrode.

13. An assembly in accordance with claim 10 wherein said distal tube includes a flared proximal end that contacts a cavity inner surface of at least one of said manifold body and said electrode.

14. An irrigated ablation catheter comprising:
- a tubular catheter body comprising an inner tubular member and an outer tubular member, said catheter body comprising a proximal portion and a distal portion;
- an electrode positioned partially within, and extending from, said distal portion of said catheter body;
- a flow member positioned at least partially within said distal portion of said catheter body; and
- a flow path extending through said catheter body and said member to an outside of said catheter, said flow path being configured to provide cooling fluid to an external surface of said electrode.

15. A catheter in accordance with claim 14 further comprising a middle tubular member having a distal end attached to a distal end of said outer tubular member, said flow path extending between said inner tubular member and said middle tubular member.

16. A catheter in accordance with claim 15 wherein said electrode is attached to a distal end of said inner tubular member, said flow distributor positioned at said middle tubular member distal end.

17. A catheter in accordance with claim 15 wherein said middle tubular member distal end contacts an outer surface of said flow member and an inner surface of said outer tubular member.

18. A catheter in accordance with claim 15 further comprising a seal member configured to transfer the fluid from an inner fluid delivery lumen to the space between said inner tubular member and said middle tubular member.

19. A catheter in accordance with claim 14 wherein said electrode further comprises a temperature sensor, said catheter further comprising at least one sensing ring located on an external surface of said outer tubular member.

20. A catheter in accordance with claim 14 further comprising an insulation member positioned on a proximal portion of said electrode, said insulation member having an inner surface and an outer surface, said inner surface contacting said electrode, said outer surface contacting said flow member.

21. A catheter in accordance with claim 14 wherein said catheter includes an axis and said flow distributor includes a plurality of channels extending therethrough, said channels being oriented at least one of substantially parallel to said axis and circumferentially displaced from a first end to a second end thereof.

22. A catheter in accordance with claim 14 wherein a gap extends between an outer surface of said electrode and an inner surface of said outer tubular member.

23. A catheter in accordance with claim 22 wherein the gap further extends from a distal end of said flow member.

24. A method of assembling an electrode assembly for an ablation catheter, the assembly including an electrode, a manifold body, and a distal tube, said method comprising:
- loading the distal tube onto a mandrel;
- inserting the mandrel and the distal tube through a distal cavity of the manifold body until a proximal end of the distal tube is positioned adjacent an end of the distal cavity; and
- positioning the electrode over the mandrel and the distal tube.

25. A method in accordance with claim 24 wherein positioning the electrode comprises positioning the electrode such that an electrode proximal end contacts a distal end of a middle portion of the manifold.

26. A method in accordance with claim 24 further comprising:
- positioning a portion of the manifold body within a cavity of the electrode;
- positioning the distal tube such that it extends from the manifold body and through the electrode;
- applying an adhesive to the distal tube; and
- removing the mandrel from within the distal tube and the electrode.

* * * * *